United States Patent
Kang et al.

(10) Patent No.: US 10,485,781 B2
(45) Date of Patent: Nov. 26, 2019

(54) AMINOCARBONYLCARBAMATE COMPOUNDS

(71) Applicant: SK BIOPHARMACEUTICALS CO., LTD., Gyeonggi-do (KR)

(72) Inventors: Young-Soon Kang, Daejeon (KR); Jin-Yong Chung, Daejeon (KR); Cheol-Young Maeng, Daejeon (KR); Han-Ju Yi, Daejeon (KR); Ki-Ho Lee, Daejeon (KR); Joon Heo, Daejeon (KR); Eun-Hee Chae, Daejeon (KR); Yu-Jin Shin, Daejeon (KR)

(73) Assignee: SK BIOPHARMACEUTICALS CO., LTD., Gyeonggi-do (KR)

(*) Notice: Subject to any disclaimer, the term of this patent is extended or adjusted under 35 U.S.C. 154(b) by 0 days.

(21) Appl. No.: 16/395,422

(22) Filed: Apr. 26, 2019

(65) Prior Publication Data
US 2019/0247356 A1 Aug. 15, 2019

Related U.S. Application Data

(60) Continuation of application No. 15/805,293, filed on Nov. 7, 2017, now Pat. No. 10,314,808, which is a continuation of application No. 15/195,326, filed on Jun. 28, 2016, now Pat. No. 9,833,432, which is a division of application No. 14/633,388, filed on Feb. 27, 2015, now Pat. No. 9,403,761.

(60) Provisional application No. 61/946,142, filed on Feb. 28, 2014.

(51) Int. Cl.
A61K 31/325 (2006.01)
A61P 25/00 (2006.01)
A61K 31/27 (2006.01)
C07C 275/60 (2006.01)
A61K 45/06 (2006.01)
A61K 9/00 (2006.01)

(52) U.S. Cl.
CPC .......... A61K 31/325 (2013.01); A61K 9/0053 (2013.01); A61K 31/27 (2013.01); A61K 45/06 (2013.01); A61P 25/00 (2018.01); C07C 275/60 (2013.01)

(58) Field of Classification Search
CPC .... C07C 275/60; A61K 31/325; A61K 9/0053
See application file for complete search history.

(56) References Cited

U.S. PATENT DOCUMENTS

| 5,077,289 | A | 12/1991 | Glamkowski et al. |
| 5,705,640 | A | 1/1998 | Choi et al. |
| 5,756,817 | A | 5/1998 | Choi et al. |
| 5,955,499 | A | 9/1999 | Choi et al. |
| 6,140,532 | A | 10/2000 | Choi et al. |
| 8,232,315 | B2 | 7/2012 | Lee et al. |
| 8,741,950 | B2 | 6/2014 | Khayrallah et al. |
| 9,403,761 | B2* | 8/2016 | Kang ............ C07C 275/60 |
| 9,833,432 | B2* | 12/2017 | Kang ............ C07C 275/60 |
| 10,314,808 | B2* | 6/2019 | Kang ............ C07C 275/60 |
| 2005/0080268 | A1 | 4/2005 | Choi et al. |
| 2006/0058548 | A1 | 3/2006 | Choi et al. |
| 2008/0039529 | A1 | 2/2008 | Sporn |
| 2009/0221553 | A1 | 9/2009 | Palumbo et al. |
| 2009/0312416 | A1 | 12/2009 | Ahnaou et al. |
| 2012/0004300 | A1 | 1/2012 | Lee et al. |
| 2012/0004301 | A1 | 1/2012 | Melnick et al. |
| 2012/0245226 | A1 | 9/2012 | Lee et al. |
| 2012/0252892 | A1 | 10/2012 | Lee et al. |
| 2013/0137764 | A1 | 5/2013 | Ahnaou et al. |
| 2018/0085337 | A1 | 3/2018 | Kang et al. |

OTHER PUBLICATIONS

Berge et al. "*Pharmaceutical Salts*", J. Pharm. Sci., 1977; 66(1): 1-19.
Hitri et al., "*Molecular, Functional and Biochemical Characteristics of the Dopamine Transporter: Regional Differences and Clinical Relevance*", 1994, Clin. Pharmacol. 17:1-22.
Hoffman et al., "*Localization and Dynamic Regulation of Biogenic Amine Transporters in the Mammalian Central Nervous System*" 1998, Front. Neuroendocrinol. 19(3):187-231.
Javitch et al., "*[3H]Mazindol Binding Associated with Neuronal Dopamine and Norepinephrine Uptake Sites*", 1984, Mol. Pharmacol. 26(1):35-44.
Lowry et al., "*Protein Measurement With the Folin Phenol Reagent*\**", 1951, J. Biol. Chem. 193:265-275.
Madras et al., "*Cocaine Receptors Labeled by [3H]2β-Carbomethoxy-3β-(4-fluorophenyl) tropane*", May 24, 1989, Mol. Pharmacol. 36(4):518-524.
Office Action (Non-Final Rejection) dated Dec. 23, 2016 in U.S. Appl. No. 15/195,326.

(Continued)

Primary Examiner — Pancham Bakshi
(74) Attorney, Agent, or Firm — Harness, Dickey & Pierce, P.L.C.

(57) ABSTRACT

The present disclosure provides a compound represented by Formula (I) and a pharmaceutically acceptable salt which are effective as a dopamine reuptake inhibitor and a method of using the compound:

wherein X is independently halo, alkyl, alkoxy or nitro; m is 0, 1, 2, 3 or 4; n is 1 or 2; $R_1$ and $R_2$ are independently H— or alkyl; $R_3$ is H—, alkyl or aralkyl; and $R_4$ is H— or aryl.

18 Claims, No Drawings

(56) References Cited

OTHER PUBLICATIONS

Office Action (Non-Final Rejection) dated Mar. 1, 2018 in U.S. Appl. No. 15/805,291.
Office Action (Final Rejection) dated Oct. 12, 2018 in U.S. Appl. No. 15/805,291.

* cited by examiner

AMINOCARBONYLCARBAMATE COMPOUNDS

CROSS-REFERENCE TO RELATED APPLICATIONS

This application is a continuation application of U.S. application Ser. No. 15/805,293, filed 7 Nov. 2017, which is a continuation application of U.S. application Ser. No. 15/195,326, filed on 28 Jun. 2016, now U.S. Pat. No. 9,833,432, which is a divisional application of U.S. application Ser. No. 14/633,388, filed on 27 Feb. 2015, now U.S. Pat. No. 9,403,761, which claims the benefit and priority to Provisional Application No. 61/946,142, filed on 28 Feb. 2014. The entire disclosures of the applications identified in this paragraph are incorporated herein by reference.

FIELD

The present disclosure generally relates to a compound having inhibitory activity, pharmaceutical compositions comprising the compound, methods of using the compound for treating diseases and processes for preparing the same. More particularly, the present disclosure relates to aminocarbonylcarbamate compounds and pharmaceutically acceptable salts thereof useful as dopamine reuptake inhibitor and/or a psycho-stimulant.

BACKGROUND

Dopamine is a monoamine neurotransmitter that plays a critical role in the function of the hypothalamic-pituitary-adrenal axis and in the integration of information in sensory, limbic, and motor systems. The primary mechanism for termination of dopamine neurotransmission is through reuptake of released dopamine by $Na^+/Cl^-$-dependent plasma membrane transporter (Hoffman et al., 1998, *Front. Neuroendocrinol.* 19(3):187-231). Depending on the surrounding ionic conditions, the dopamine transporter can function as a mediator of both inward directed dopamine transport (i.e., "reuptake") and outward directed dopamine transport (i.e., "release"). The functional significance of the dopamine transporter is its regulation of dopamine neurotransmission by terminating the action of dopamine in a synapse via reuptake (Hitri et al., 1994, *Clin. Pharmacol.* 17:1-22)

The outcome of inhibiting dopamine reuptake is an increase in the concentration of dopamine and of 3-methoxytyramine (3MT) in the synaptic space without modifying the concentrations of 3,4-dihydroxyphenylacetic acid (DOPAC) and of homovanillic acid (HVA). This property manifests itself in an increase in the functioning of the central dopaminergic pathways, which is appraised objectively by behavioral modifications such as the appearance of stereotyped movements, an increase in locomotor activity and a reduction in the period of immobility in animals subjected to the test of "behavioral despair."

As a result of their properties of inhibition of dopamine reuptake, the compounds may be used in various indications including a hyperkinetic disorder such as attention deficit hyperactivity disorder (ADHD).

These indications, in many cases, involve a deficiency of functioning of the central dopaminergic systems. Therefore, dopamine reuptake inhibition can lead to economical use of the synthesized/released dopamine which may result in an improvement in dopaminergic transmissions.

The tenth edition of *the International Statistical Classification of Diseases and Related Health Problems* (ICD-10), 2010 provides classifications of mental and behavioral disorders in Chapter V in which signs of ADHD are classified under "hyperkinetic disorders." Hyperkinetic disorders are defined therein as a group of disorders characterized by an early onset, lack of persistence in activities that require cognitive involvement, and a tendency to move from one activity to another without completing any one, together with disorganized, ill-regulated, and excessive activity. Hyperkinetic disorders (F90) include the following subclasses of disorders:

F90.0 Disturbance of activity and attention,
F90.1 Hyperkinetic conduct disorder
F90.8 Other hyperkinetic disorders
F90.9 Hyperkinetic disorder, unspecified.

Phenylethylamine derivatives are a class of therapeutical medicines useful for managing central nervous system (CNS) diseases.

For example, U.S. Pat. Nos. 5,705,640 and 5,756,817 describe that carbamate compounds represented by the following formula are effective in treating CNS disorders.

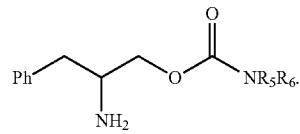

U.S. Pat. No. 5,077,289 mentions aminocarbonylcarbamate compounds useful for enhancing cholinergic functions and as analgesic agents.

SUMMARY

The present disclosure provides a novel compound represented by Formula (I) and a pharmaceutical acceptable salt thereof:

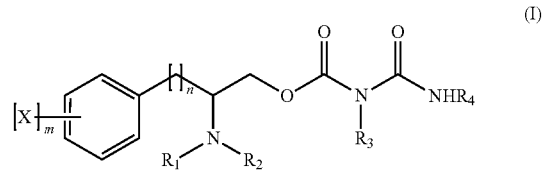

wherein:

X is independently halo, alkyl, alkoxy or nitro;

m is 0, 1, 2, 3 or 4 n is 1 or 2;

$R_1$ and $R_2$ are independently H— or alkyl;

$R_3$ is H—, alkyl or aralkyl; and $R_4$ is H— or aryl, wherein at least one of $R_1$, $R_2$, $R_3$ and $R_4$ is not H—.

The compounds of Formula (I) are useful in inhibiting dopamine reuptake.

In some embodiments, a compound of Formula (I) is selected from a compound of Formula (II) and a pharmaceutical acceptable salt thereof:

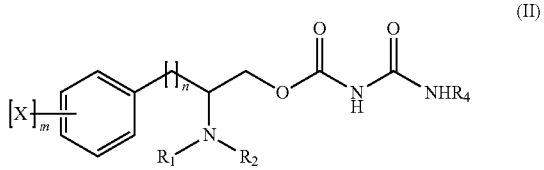

wherein X, m, n, $R_1$, $R_2$, and $R_4$ are as defined above.

In some embodiments, a compound of Formula (I) is selected from a compound of Formula (III) and a pharmaceutical acceptable salt thereof:

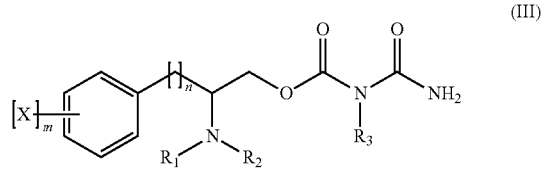

wherein X, m, n, $R_1$, $R_2$, and $R_3$ are as defined above.

In another embodiment, there is provided a pharmaceutical composition comprising a therapeutically effective amount of one or more compounds described herein and a pharmaceutically acceptable carrier.

In yet another embodiment, there is provided a method of treating dopamine reuptake-related diseases in a mammal in need thereof by administering a therapeutically effective amount of the compound represented by Formula (I), (II) or (III). In an embodiment, the dopamine reuptake-related disease is attention deficit hyperactivity disorder (ADHD).

DETAILED DESCRIPTION

The following description is merely exemplary in nature and is not intended to limit the present disclosure, application, or uses.

Definitions

"Alkoxy" is RO— where R is alkyl. Non-limiting examples of alkoxy groups include methoxy, ethoxy and propoxy.

"Alkyl" refers to a straight or branched chain saturated hydrocarbyl group. In an embodiment, alkyl has from 1 to 12 carbon atoms. In some embodiments, alkyl is a $C_1$-$C_{10}$ alkyl group or a $C_1$-$C_4$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Aryl" refers to a monocyclic, bicyclic, or tricyclic carbon ring, wherein at least one ring is aromatic. In an embodiment, aryl has from 6 to 12 carbon atoms. In some embodiments, aryl is a $C_6$-$C_{10}$ aryl group.

"Aralkyl" refers to an alkyl group substituted with an aryl group.

"Halo" refers to chloro (—Cl), bromo (—Br), fluoro (—F) or iodo (—I).

"Pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically acceptable carrier" refers to a diluent, adjuvant, excipient, or carrier that alone or together provides a carrier or vehicle with which a compound or compounds of the disclosure is formulated and/or administered, and in which every ingredient or the carrier as a whole is pharmaceutically acceptable.

"Pharmaceutically acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Embraced herein, where applicable, are permissible isomers such as tautomers, racemates, enantiomers, diastereomers, atropisomers, and isotopic variants. In various embodiments, the compounds of Formula (I) are enantiomers.

Compounds

This disclosure provides a compound represented by Formula (I) and a pharmaceutical acceptable salt:

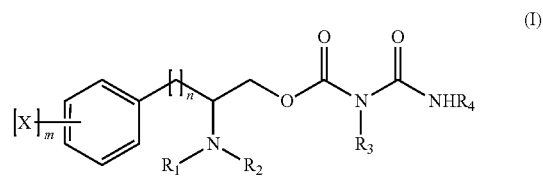

wherein:
X is independently halo, alkyl, alkoxy or nitro;
m is 0, 1, 2, 3 or 4;
n is 1 or 2;
$R_1$ and $R_2$ are independently H— or alkyl;
$R_3$ is H—, alkyl or aralkyl; and
$R_4$ is H— or aryl,
wherein at least one of $R_1$, $R_2$, $R_3$ and $R_4$ is not H—.

In an embodiment, X is halo, $C_1$-$C_4$ alkyl, $C_1$-$C_4$ alkoxy or nitro; $R_1$ and $R_2$ are independently H— or $C_1$-$C_4$ alkyl; $R_3$ is H—, $C_1$-$C_4$ alkyl or $C_6$-$C_{10}$ aryl-$C_1$-$C_4$ alkyl; and $R_4$ is H— or $C_6$-$C_{10}$ aryl.

X is one or more substituents attached to the phenyl group of Formula (I) where m is a number of X substitutions. Thus, the phenyl group has up to 4 substituents selected from X. In an embodiment, X is independently selected from halo, methyl, tert-butyl, ethoxy and nitro.

n represents a number of carbon atom(s) of the alkylene linker; in other words, n=1 and n=2 represent —$CH_2$— and —$CH_2CH_2$—, respectively.

In an embodiment, $R_1$ and $R_2$ are independently H—, methyl or isopropyl.

In an embodiment, $R_3$ is methyl, ethyl or benzyl. In a particular embodiment, $R_3$ is methyl.

In an embodiment, $R_4$ is H— or phenyl. In a particular embodiment, $R_4$ is H—.

In particular embodiments, compounds of Formula (I) include, but not limited to, the following compounds.

2-(isopropylamino)-3-phenylpropyl (aminocarbonyl)carbamate;
2-(dimethylamino)-3-phenylpropyl (aminocarbonyl)carbamate;
2-amino-3-(2-chlorophenyl)propyl (aminocarbonyl)carbamate;
2-amino-3-(2,4-dichlorophenyl)propyl (aminocarbonyl)carbamate;
2-amino-3-(3,4-dichlorophenyl)propyl (aminocarbonyl)carbamate;
2-amino-3-phenylpropyl (aminocarbonyl)methylcarbamate;
2-amino-3-(4-chlorophenyl)propyl (aminocarbonyl)carbamate;
2-amino-3-(3-chlorophenyl)propyl (aminocarbonyl)carbamate;
2-amino-3-(4-nitrophenyl)propyl (aminocarbonyl)carbamate;
2-amino-3-(4-tert-butylphenyl)propyl (aminocarbonyl)carbamate;
2-amino-3-(2-fluorophenyl)propyl (aminocarbonyl)carbamate;
2-(methylamino)-3-phenylpropyl (aminocarbonyl)carbamate;
2-(dimethylamino)-3-phenylpropyl (aminocarbonyl)methylcarbamate;
2-amino-3-phenylpropyl (aminocarbonyl)benzylcarbamate;
2-amino-3-phenylpropyl (aminocarbonyl)ethylcarbamate;
2-amino-3-(2-chlorophenyl)propyl (aminocarbonyl)methylcarbamate;
2-amino-3-(4-fluorophenyl)propyl (aminocarbonyl)methylcarbamate;
2-amino-3-(4-chlorophenyl)propyl (aminocarbonyl)methylcarbamate;
2-amino-3-(2,4-dichlorophenyl)propyl (aminocarbonyl)methylcarbamate;
2-amino-3-(3,4-dichlorophenyl)propyl (aminocarbonyl)methylcarbamate;
2-amino-3-phenylpropyl (aminocarbonyl)methylcarbamate;
2-amino-3-(4-nitrophenyl)propyl (aminocarbonyl)methylcarbamate;
2-amino-3-(4-methylphenyl)propyl (aminocarbonyl)methylcarbamate;
2-amino-3-(4-ethoxyphenyl)propyl (aminocarbonyl)methylcarbamate;
2-amino-4-phenylbutyl (aminocarbonyl)methylcarbamate; and
2-amino-3-phenylpropyl (anilinocarbonyl)carbamate.

Compounds of Formula (I) include all permissible isomers such as racemates, enantiomers, diastereomers and isotopic variants. In some embodiments, a compound of Formula (I) is a stereoisomer. In a particular embodiment, the stereoisomer is substantially enantiopure, for example consisting essentially of the R enantiomer of the compound. Examples of enantiomeric compounds include, but are not limited to, the following compounds:

(2R)-2-(isopropylamino)-3-phenylpropyl (aminocarbonyl)carbamate;
(2R)-2-(dimethylamino)-3-phenylpropyl (aminocarbonyl)carbamate;
(2R)-2-amino-3-(2-chlorophenyl)propyl (aminocarbonyl)carbamate;
(2R)-2-amino-3-(2,4-dichlorophenyl)propyl (aminocarbonyl)carbamate;
(2R)-2-amino-3-(3,4-dichlorophenyl)propyl (aminocarbonyl)carbamate;
(2R)-2-amino-3-phenylpropyl (aminocarbonyl)methylcarbamate;
(2R)-2-(methylamino)-3-phenylpropyl (aminocarbonyl)carbamate;
(2R)-2-(dimethylamino)-3-phenylpropyl (aminocarbonyl)methylcarbamate;
(2R)-2-amino-3-phenylpropyl (aminocarbonyl)benzylcarbamate;
(2R)-2-amino-3-phenylpropyl (aminocarbonyl)ethylcarbamate;
(2R)-2-amino-3-(2-chlorophenyl)propyl (aminocarbonyl)methylcarbamate;
(2R)-2-amino-3-(4-chlorophenyl)propyl (aminocarbonyl)methylcarbamate;
(2R)-2-amino-3-(2,4-dichlorophenyl)propyl (aminocarbonyl)methylcarbamate;
(2R)-2-amino-3-(3,4-dichlorophenyl)propyl (aminocarbonyl)methylcarbamate;
(2S)-2-amino-3-phenylpropyl (aminocarbonyl)methylcarbamate;
(2R)-2-amino-3-(4-nitrophenyl)propyl (aminocarbonyl)methylcarbamate;
(2R)-2-amino-3-(4-methylphenyl)propyl (aminocarbonyl)methylcarbamate;
(2R)-2-amino-3-(4-ethoxyphenyl)propyl (aminocarbonyl)methylcarbamate;
(2R)-2-amino-4-phenylbutyl (aminocarbonyl)methylcarbamate; and
(2R)-2-amino-3-phenylpropyl (anilinocarbonyl)carbamate.

In another embodiment, there is provided a compound of Formula (II) or a pharmaceutically acceptable salt thereof:

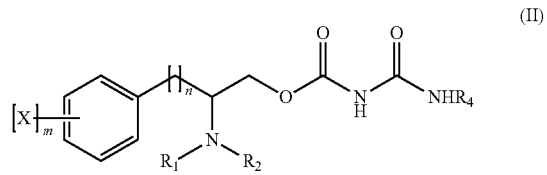

wherein X, m, n, $R_1$, $R_2$, and $R_4$ are as defined above and at least one of $R_1$, $R_2$ and $R_4$ is not H—.

In an embodiment, X is halo, $C_1$-$C_4$ alkyl, $C_1$-$C_4$ alkoxy or nitro; $R_1$ and $R_2$ are independently H— or $C_1$-$C_4$ alkyl; and $R_4$ is H— or $C_6$-$C_{10}$ aryl.

In an embodiment, X is independently halo, methyl, tert-butyl, ethoxy or nitro. In a particular embodiment, X is chloro, fluoro, methyl, tert-butyl, ethoxy or nitro.

In an embodiment, $R_1$ and $R_2$ are independently H—, methyl or isopropyl. In particular embodiments, $R_1$ is methyl and $R_2$ is H—; $R_1$ is methyl and $R_2$ is methyl; or $R_1$ is isopropyl and $R_2$ is H—.

In an embodiment, $R_4$ is H— or phenyl.

Examples of Formula (II) includes, but are not limited to, the following compounds:
2-(isopropylamino)-3-phenylpropyl (aminocarbonyl)carbamate;
2-(dimethylamino)-3-phenylpropyl (aminocarbonyl)carbamate;
2-amino-3-(2-chlorophenyl)propyl (aminocarbonyl)carbamate;
2-amino-3-(2,4-dichlorophenyl)propyl (aminocarbonyl)carbamate;
2-amino-3-(3,4-dichlorophenyl)propyl (aminocarbonyl)carbamate;
2-amino-3-(4-chlorophenyl)propyl (aminocarbonyl)carbamate;
2-amino-3-(3-chlorophenyl)propyl (aminocarbonyl)carbamate;
2-amino-3-(4-nitrophenyl)propyl (aminocarbonyl)carbamate;
2-amino-3-(4-tert-butylphenyl)propyl (aminocarbonyl)carbamate;
2-amino-3-(2-fluorophenyl)propyl (aminocarbonyl)carbamate;
2-(methylamino)-3-phenylpropyl (aminocarbonyl)carbamate; and
2-amino-3-phenylpropyl (anilinocarbonyl)carbamate.

Compounds of Formula (II) include all permissible isomers. In some embodiment, a compound of Formula (II) is an enantiomer. In a particular embodiment, the stereoisomer is substantially enantiopure, for example consisting essentially of the R enantiomer of the compound. Examples of enantiomers include, but are not limited to, the following compounds:
(2R)-2-(isopropylamino)-3-phenylpropyl (aminocarbonyl)carbamate;
(2R)-2-(dimethylamino)-3-phenylpropyl (aminocarbonyl)carbamate;
(2R)-2-amino-3-(2-chlorophenyl)propyl (aminocarbonyl)carbamate;
(2R)-2-amino-3-(2,4-dichlorophenyl)propyl (aminocarbonyl)carbamate;
(2R)-2-amino-3-(3,4-dichlorophenyl)propyl (aminocarbonyl)carbamate;
(2R)-2-(methylamino)-3-phenylpropyl (aminocarbonyl)carbamate; and
(2R)-2-amino-3-phenylpropyl (anilinocarbonyl)carbamate.

In yet another embodiment, there is provided a compound of Formula (III) or a pharmaceutically acceptable salt thereof:

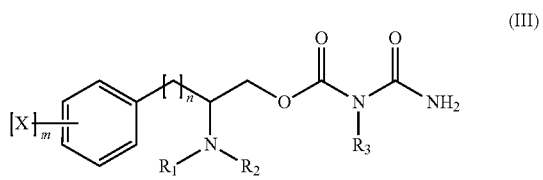

(III)

wherein X, m, n, $R_1$, $R_2$, and $R_3$ are as defined above at least one of $R_1$, $R_2$ and $R_3$ is not H—.

In an embodiment, X is halo, $C_1$-$C_4$ alkyl, $C_1$-$C_4$ alkoxy or nitro; $R_1$ and $R_2$ are independently H— or $C_1$-$C_4$ alkyl; and $R_3$ is H—, $C_1$-$C_4$ alkyl or $C_6$-$C_{10}$ aryl-$C_1$-$C_4$ alkyl.

In an embodiment, X is independently halo, methyl, tert-butyl, ethoxy or nitro. In a particular embodiment, X is chloro, fluoro, methyl, tert-butyl, ethoxy or nitro.

In an embodiment, $R_1$ and $R_2$ are independently H—, methyl or isopropyl.

In an embodiment, $R_3$ is H—, $C_1$-$C_4$ alkyl or $C_6$-$C_{10}$ aryl-$C_1$-$C_4$ alkyl, particularly methyl, ethyl or benzyl. In a particular embodiment, $R_3$ is methyl.

Examples of Formula (III) includes, but are not limited to, the following compounds:
2-amino-3-phenylpropyl (aminocarbonyl)methylcarbamate;
2-(dimethylamino)-3-phenylpropyl (aminocarbonyl)methylcarbamate;
2-amino-3-phenylpropyl (aminocarbonyl)benzylcarbamate;
2-amino-3-phenylpropyl (aminocarbonyl)ethylcarbamate;
2-amino-3-(2-chlorophenyl)propyl (aminocarbonyl)methylcarbamate;
2-amino-3-(4-fluorophenyl)propyl (aminocarbonyl)methylcarbamate;
2-amino-3-(4-chlorophenyl)propyl (aminocarbonyl)methylcarbamate;
2-amino-3-(2,4-dichlorophenyl)propyl (aminocarbonyl)methylcarbamate;
2-amino-3-(3,4-dichlorophenyl)propyl (aminocarbonyl)methylcarbamate;
2-amino-3-(4-nitrophenyl)propyl (aminocarbonyl)methylcarbamate;
2-amino-3-(4-methylphenyl)propyl (aminocarbonyl)methylcarbamate;
2-amino-3-(4-ethoxyphenyl)propyl (aminocarbonyl)methylcarbamate; and
2-amino-4-phenylbutyl (aminocarbonyl)methylcarbamate.

Compounds of Formula (III) include all permissible isomers. In some embodiment, a compound of Formula (III) is an enantiomer. In a particular embodiment, the stereoisomer is substantially enantiopure, for example consisting essentially of the R enantiomer of the compound. Examples of enantiomers include, but are not limited to, the following compounds:
(2R)-2-amino-3-phenylpropyl (aminocarbonyl)methylcarbamate;
(2R)-2-(dimethylamino)-3-phenylpropyl (aminocarbonyl)methylcarbamate;
(2R)-2-amino-3-phenylpropyl (aminocarbonyl)benzylcarbamate;
(2R)-2-amino-3-phenylpropyl (aminocarbonyl)ethylcarbamate;
(2R)-2-amino-3-(2-chlorophenyl)propyl (aminocarbonyl)methylcarbamate;
(2R)-2-amino-3-(4-chlorophenyl)propyl (aminocarbonyl)methylcarbamate;
(2R)-2-amino-3-(2,4-dichlorophenyl)propyl (aminocarbonyl)methylcarbamate;
(2R)-2-amino-3-(3,4-dichlorophenyl)propyl (aminocarbonyl)methylcarbamate;
(2S)-2-amino-3-phenylpropyl (aminocarbonyl)methylcarbamate;
(2R)-2-amino-3-(4-nitrophenyl)propyl (aminocarbonyl)methylcarbamate;
(2R)-2-amino-3-(4-methylphenyl)propyl (aminocarbonyl)methylcarbamate;

(2R)-2-amino-3-(4-ethoxyphenyl)propyl (aminocarbonyl) methylcarbamate; and (2R)-2-amino-4-phenylbutyl (aminocarbonyl)methylcarbamate.

In yet another embodiment, there is provided 2-amino-3-phenylpropyl (aminocarbonyl)carbamate or a pharmaceutically acceptable salt thereof. In some embodiment, the compound is an enantiomer of 2-amino-3-phenylpropyl (aminocarbonyl)carbamate, such as, (2R)-2-amino-3-phenylpropyl (aminocarbonyl)carbamate.

Synthesis of Compounds

In some embodiments, the compounds of Formula (I) can be prepared by the synthetic method of Scheme I or II, as described below.

It should be noted that the stereochemistry of the final products (I) depend solely on that of the starting material (II); a starting material (II) with an S-enantiomer yields only a product with S-enantiomer (I) and a starting material (II) with an R-enantiomer yields only a product with R-enantiomer (I).

When $R_3$ and $R_4$ are H—, the desired compound may be prepared by the synthetic method described in Scheme I:

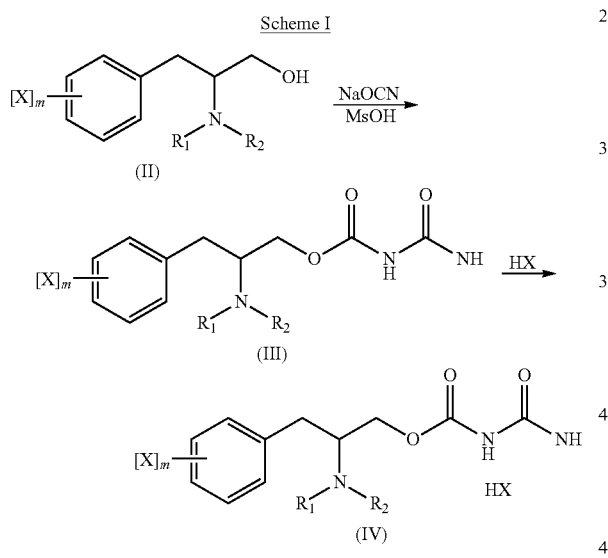

As shown in Scheme I, 2-amino-3-phenylpropan-1-ol (II) is reacted with sodium cyanate and methansulfonic acid in dichloromethane, to give 2-amino-3-phenylpropyl (aminocarbonyl)carbamate (III).

Details of the reaction conditions described in Scheme I are as follows. For the conversion of the compounds (II) to the compound (III), the concentration of the starting material (II) is between about 0.05 to 0.1 mole with sodium cyanate from about 6 equivalents and methanesulfonic acid from about 7 equivalents. This reaction is preferably carried out in dichloromethane at a temperature of 0° C. to room temperature.

In the Scheme I, HX represents an acid capable of forming a pharmacologically useful salt with the basic nitrogen atom. Specific examples of the anhydrous acid used for the preparation of the compound (IV) from the compound (III) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid and the like. Additional acids can refer to "Pharmaceutical Salts", *J. Pharm. Sci.,* 1977; 66(1): 1-19. This preparation is executed in a reaction media which can be exemplified by an ethereal solvent such as THF, an alcoholic solvent such as methanol, an ester solvent such as ethyl acetate, and aromatic solvent, and any compositional mixture thereof. An ethereal solvent is recommended as an addition solution, including ethyl ether, propyl ether, isopropyl ether, butyl ether, isobutyl ether.

When $R_3$ is not H— and $R_4$ is H—, the desired compound may be prepared by the synthetic method described in Scheme II:

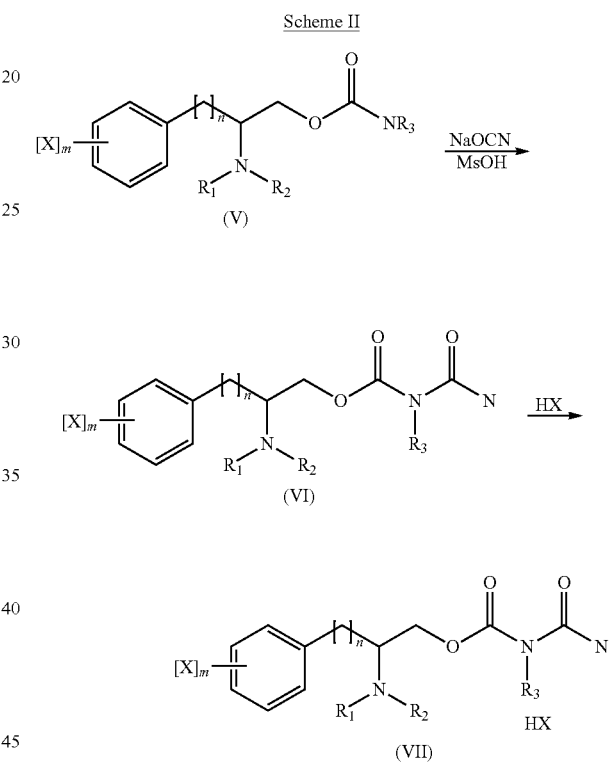

As shown in Scheme II, 2-amino-3-phenylpropyl carbamate (V) is reacted with sodium cyanate and methansulfonic acid in dichloromethane, to give 2-amino-3-phenylpropyl (aminocarbonyl)carbamate (VI).

Details of the reaction conditions described in Scheme II are as follows. For the conversion of the compounds (V) to the compound (VI), the concentration of the starting material (II) is between about 0.05 to 0.1 mole with sodium cyanate from about 4 equivalents and methanesulfonic acid from about 5 equivalents. This reaction is preferably carried out in dichloromethane at a temperature of 0° C. to room temperature.

In the Scheme II, HX represents an acid capable of forming a pharmacologically useful salt with the basic nitrogen atom.

When $R_3$ and $R_4$ are not H—, the desired compound may be prepared by the synthetic method described in Scheme III:

Scheme III

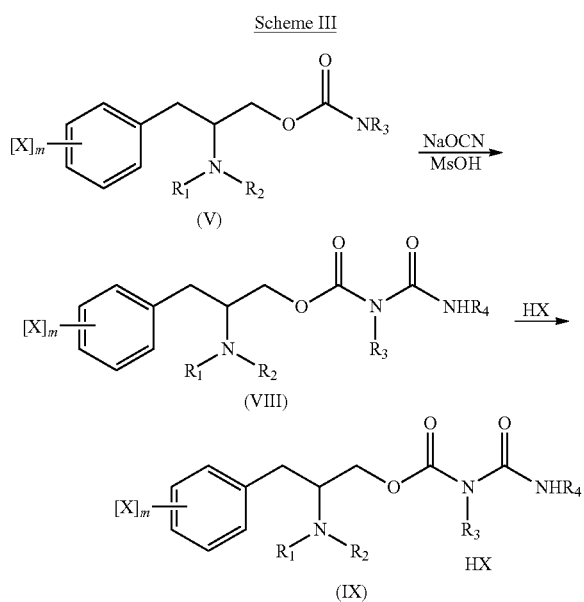

As shown in Scheme III, 2-amino-3-phenylpropyl carbamate (V) is reacted with and isocyanate of the formula $R_4NCO$ to give 2-amino-3-phenylpropyl (aminocarbonyl) carbamate (VIII).

Details of the reaction conditions described in Scheme III are as follows. For the conversion of the compounds (V) to the compound (VIII), the concentration of the starting material (II) is between about 0.05 to 0.1 moles with isocyanate, $R_4NCO$ from about 6 equivalents and methanesulfonic acid from about 3 equivalents. This reaction is preferably carried out in dichloromethane at a temperature of 0° C. to room temperature.

In the Scheme III, HX represents an acid capable of forming a pharmacologically useful salt with the basic nitrogen atom.

Pharmaceutical Compositions

In one embodiment, there is provided a pharmaceutical composition comprising, in addition to one or more compounds described herein, a pharmaceutically acceptable carrier. In various embodiments, the carrier comprises a diluent, adjuvant, excipient, other additive, or a combination of additive that separately or together provide a carrier in which the compositions can be formulated or administered. The composition can take any suitable form for the desired route of administration. Where the composition is to be administered orally, any suitable orally deliverable dosage form can be used, including, without limitation, tablets, capsules (solid- or liquid-filled), powders, granules, syrups and other liquids, elixirs, inhalants, troches, lozenges, and solutions. Injectable compositions or iv infusions are also provided in the form of solutions, suspensions, and emulsions.

In particular embodiments, the pharmaceutical composition is an oral formulation. Since the compounds of Formula I absorb well orally, it is generally unnecessary to resort to parenteral administration. For oral administration, the compound is preferably formulated with a pharmaceutically acceptable carrier. The ratio of the carrier to the compound would not be critical to the pharmacological effects of the formulation, and the ratio can vary considerably depending on formulating conditions. In tableting, various edible pharmaceutical carriers or the mixture thereof can be included therein. A suitable carrier, for example, is a mixture of lactose, dibasic calcium phosphate and/or corn starch. Other pharmaceutically acceptable ingredients can be further added, including lubricants such as magnesium stearate.

A pharmaceutical composition according to the present disclosure may contain one or more additional therapeutic agents, for example, to increase the efficacy or decrease the side effects. In an embodiment, the pharmaceutical composition includes one or more active ingredients effective to treat ADHD such as Adderall, Concerta, Dexedrine, Focalin, Metadate, Methylin, Ritalin, Vyvanse, Daytrana, and Quillivant.

Medical Utilities

Yet another aspect of the present disclosure is to provide a method of inhibiting or treating dopamine reuptake-related diseases in animal, comprising administering to said animal a therapeutically effective amount of one or more compounds of Formula (I) and salts thereof. The dopamine reuptake-related diseases include, for example, hyperkinetic disorders such as ADHD. In one embodiment, the method of inhibiting or treating disease comprises administering to an animal a pharmaceutical composition comprising an effective amount of one or more compounds of Formula (I) and a pharmaceutically-acceptable carrier.

A method of the present disclosure is particularly suitable for use with humans, but may be used with other animals, particularly mammals.

In ADHD therapies, psychostimulants reduce excess motor activity and enhance concentration. The reduction in physical activity in ADHD patients after psychostimulant treatment is supported by studies using subjective rating scales and objective measures such as actometers, respiration calorimetry and microwave motor activity detectors.

Primary treatment for ADHD is administration of stimulant medication, and research has focused on dopamine control. Imaging experiments have identified dopamine transporters predominantly in the caudatoputamen as methylphenidate's site of action. Single-photon emission computed tomography (SPECT) and positron emission tomography (PET) studies in ADHD patients have also demonstrated decreased metabolic activities in the basal ganglia, a region that contains high concentrations of dopamine and dopamine receptors. Assessments of catecholamine metabolites in cerebral spinal fluid of ADHD children support the imaging studies, demonstrating a positive correlation between the dopamine metabolite homovanillic acid and the degree of hyperactivity. Central dopaminergic activity is critical to the functioning of both motor and cognitive systems.

In therapeutic use as a dopamine reuptake inhibitor, the compounds of the present disclosure, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation must clinically be done and is within the skill of the art.

A better understanding of the present invention may be obtained in light of following examples which are set forth to illustrate, but are not to be construed to limit, the present invention.

EXAMPLE

Example 1: 2-Amino-3-phenylpropyl (aminocarbonyl)carbamate and hydrochloride Salt Thereof

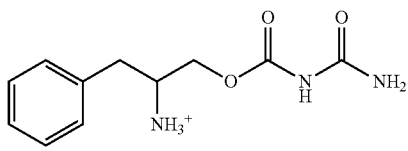 [SMILES: NC(=O)NC(=O)OCC([NH3+])Cc1ccccc1]

2-Amino-3-phenylpropan-1-ol (1.984 mmol) was dissolved in dichloromethane and methansulfonic acid (0.9 ml, 7 eq) and sodium cyanate (774 mg, 6 eq) was added in an ice bath. The resulting reaction mixture was stirred for 1 day. Water was added to terminate the reaction and the reaction mixture was neutralized to pH 7-8 with 1N NaOH solution. The organic layer was extracted 3 times with dichloromethane, dried over magnesium sulfate and concentrated in vacuo, to give oil. This was dissolved in dichloromethane and the solution was treated with a solution of HCl in ethyl ether. The resulting precipitate was filtered to give 2-amino-3-phenylpropyl (aminocarbonyl)carbamate; hydrochloride.

1H-NMR (DMSO-d6, 200 MHz) δ 9.79 (br, 1H), 8.26 (br, 3H), 7.33 (m, 5H), 7.18 (br, 2H), 4.19 (m, 1H), 3.98 (m, 1H), 3.68 (m, 1H), 2.93 (m, 2H)

Example 2: (2R)-2-Amino-3-phenylpropyl (aminocarbonyl)carbamate and hydrochloride Salt Thereof

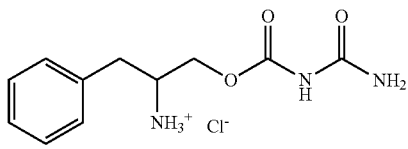 [SMILES: NC(=O)NC(=O)OCC([NH3+])Cc1ccccc1 ; [Cl-]]

The procedure given in Example 1 was followed using (2R)-2-amino-3-phenylpropan-1-ol as a reactant, instead of 2-amino-3-phenylpropan-1-ol, to give (2R)-2-amino-3-phenylpropyl (aminocarbonyl)carbamate; hydrochloride.

1H-NMR (DMSO-d6, 200 MHz) δ 9.82 (br, 1H), 8.19 (br, 3H), 7.33 (br, 5H), 7.17 (br, 2H), 4.18 (m, 1H), 3.97 (m, 1H), 3.65 (m, 1H), 2.94 (m, 2H)

Example 3: (2R)-2-(Isopropylamino)-3-phenylpropyl (aminocarbonyl)carbamate and hydrochloride Salt Thereof

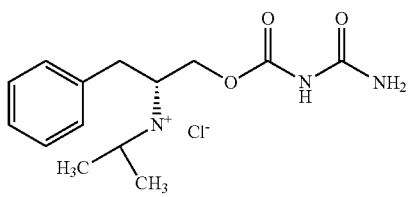 [SMILES: CC(C)[NH2+][C@@H](COC(=O)NC(N)=O)Cc1ccccc1 ; [Cl-]]

The procedure given in Example 1 was followed using (2R)-2-(isopropylamino)-3-phenylpropan-1-ol as a reactant, instead of 2-amino-3-phenylpropan-1-ol, to give (2R)-2-(isopropylamino)-3-phenylpropyl (aminocarbonyl)carbamate; hydrochloride.

1H-NMR (DMSO-d6, 200 MHz) δ 9.87 (s, 1H), 9.64 (br, 1H), 9.10 (br, 1H), 7.33 (m, 5H), 7.16 (br, 2H), 4.25 (dd, 1H), 4.04 (dd, 1H), 3.67 (br, 1H), 3.51 (br, 1H), 2.92 (dd, 1H), 2.49 (dd, 1H), 1.25 (s, 6H).

Example 4: (2R)-2-(Dimethylamino)-3-phenylpropyl (aminocarbonyl)carbamate and hydrochloride Salt Thereof

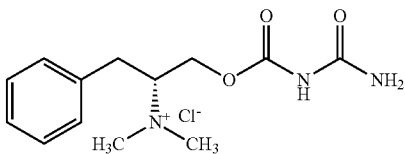 [SMILES: C[NH+](C)[C@@H](COC(=O)NC(N)=O)Cc1ccccc1 ; [Cl-]]

The procedure given in Example 1 was followed using (2R)-2-(dimethylamino)-3-phenylpropan-1-ol as a reactant, instead of 2-amino-3-phenylpropan-1-ol, to give (2R)-2-(dimethylamino)-3-phenylpropyl (aminocarbonyl)carbamate; hydrochloride.

1H-NMR (DMSO-d6, 200 MHz) δ 11.29 (br, 1H), 10.05 (s, 1H), 7.34 (m, 5H), 7.23 (br, 2H), 4.33 (dd, 1H), 3.99 (dd, 1H), 3.84 (br, 1H), 3.41 (s, 6H), 2.97 (dd, 1H), 2.94 (dd, 1H).

Example 5: (2R)-2-Amino-3-(2-chlorophenyl)propyl (aminocarbonyl)carbamate and hydrochloride Salt Thereof

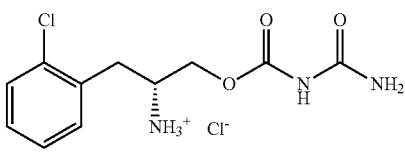 [SMILES: NC(=O)NC(=O)OC[C@H]([NH3+])Cc1ccccc1Cl ; [Cl-]]

The procedure given in Example 1 was followed using (2R)-2-amino-3-(2-chlorophenyl)propan-1-ol-HCl as a reactant, instead of 2-amino-3-phenylpropan-1-ol, to give (2R)-2-amino-3-(2-chlorophenyl)propyl (aminocarbonyl)carbamate; hydrochloride.

1H-NMR (DMSO-d6, 200 MHz) δ 9.71 (br, 1H), 8.50 (br, 3H), 7.48 (m, 2H), 7.34 (m, 2H), 7.15 (br, 2H), 4.22 (m, 1H), 4.02 (m, 1H), 3.70 (m, 1H), 3.14 (m, 2H)

Example 6: (2R)-2-Amino-3-(2,4-dichlorophenyl)propyl (aminocarbonyl)carbamate and hydrochloride Salt Thereof

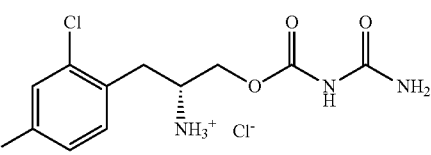

The procedure given in Example 1 was followed using (2R)-2-amino-3-(2,4-dichlorophenyl)propan-1-ol-HCl as a reactant, instead of 2-amino-3-phenylpropan-1-ol, to give (2R)-2-amino-3-(2,4-dichlorophenyl)propyl (aminocarbonyl)carbamate; hydrochloride 1H-NMR (DMSO-d6, 200 MHz) 9.82 (br, 1H), 8.23 (br, 3H), 7.66 (s, 1H), 7.49 (m, 2H), 7.18 (br, 2H), 4.26 (m, 1H), 4.00 (m, 1H), 3.64 (m, 1H), 3.09 (m, 2H)

Example 7: (2R)-2-Amino-3-(3,4-dichlorophenyl) propyl (aminocarbonyl)carbamate; Hydrochloride

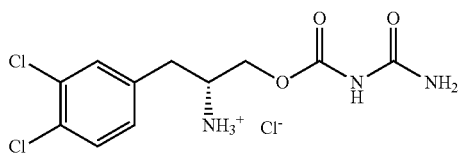 [SMILES: NC(=O)NC(=O)OC[C@H]([NH3+])Cc1ccc(Cl)c(Cl)c1 ; [Cl-]]

The procedure given in Example 1 was followed using (2R)-2-amino-3-(3,4-dichlorophenyl)propan-1-ol-HCl as a reactant, instead of 2-amino-3-phenylpropan-1-ol, to give (2R)-2-amino-3-(3,4-dichlorophenyl)propyl (aminocarbonyl)carbamate; hydrochloride 1H-NMR (DMSO-d6, 200 MHz) δ 9.82 (br, 1H), 8.25 (br, 3H), 7.65 (s, 1H), 7.62 (d, 1H), 7.34 (d, 1H), 7.18 (br, 2H), 4.26 (m, 1H), 4.00 (m, 1H), 3.72 (m, 1H), 2.96 (m, 2H)

Example 8: (2R)-2-Amino-3-phenylpropyl (aminocarbonyl)methylcarbamate and hydrochloride Salt Thereof

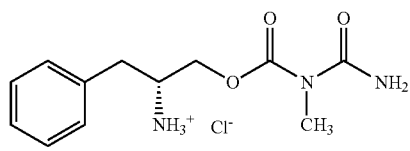 [SMILES: CN(C(N)=O)C(=O)OC[C@H]([NH3+])Cc1ccccc1 ; [Cl-]]

(2R)-2-amino-3-phenylpropyl methylcarbamate (11.932 mmol) was dissolved in dichloromethane and methansulfonic acid (3.1 ml, 4 eq) and sodium cyanate (5.39 g, 3 eq) was added in an ice bath. The resulting reaction mixture was stirred for 1 day. Water was added to terminate the reaction and the reaction mixture was basicified to pH 8-9 with 1N NaOH solution. The organic layer was extracted 3 times with dichloromethane, dried over magnesium sulfate and concentrated in vacuo, to give oil. This was dissolved in dichloromethane and the solution was treated with a solution of HCl in ethyl ether. The resulting precipitate was filtered to give (2R)-2-amino-3-phenylpropyl (aminocarbonyl)methylcarbamate; hydrochloride 1H-NMR (DMSO-d6, 200 MHz) 8.55 (br, 3H), 7.84 (br, 1H), 7.32 (m, 6H), 4.30 (dd, 1H), 4.06 (dd, 1H), 3.72 (m, 1H), 3.18 (dd, 1H), 3.14 (s, 3H), 2.90 (dd, 1H)

Example 9: 2-Amino-3-(4-chlorophenyl)propyl (aminocarbonyl)carbamate and hydrochloride Salt Thereof

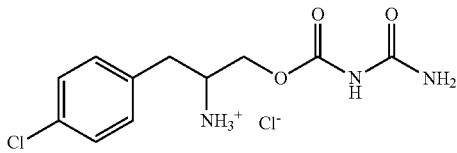 [SMILES: NC(=O)NC(=O)OCC([NH3+])Cc1ccc(Cl)cc1 ; [Cl-]]

The procedure given in Example 8 was followed using 2-amino-3-(4-chlorophenyl)propyl carbamate as a reactant, instead of (2R)-2-amino-3-phenylpropyl methylcarbamate, to give 2-amino-3-(4-chlorophenyl)propyl (aminocarbonyl)carbamate; hydrochloride.

1H-NMR (DMSO-d6, 200 MHz) δ 9.78 (br, 1H), 8.41 (br, 3H), 7.38 (m, 4H), 7.16 (br, 2H), 4.23 (m, 1H), 3.99 (m, 1H), 3.62 (m, 1H), 2.96 (m, 2H)

Example 10: 2-Amino-3-(3-chlorophenyl)propyl (aminocarbonyl)carbamate and hydrochloride Salt Thereof

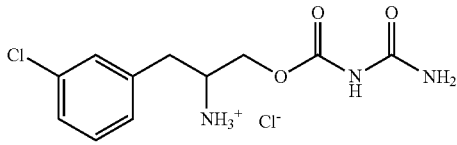 [SMILES: NC(=O)NC(=O)OCC([NH3+])Cc1cccc(Cl)c1 ; [Cl-]]

The procedure given in Example 8 was followed using 2-amino-3-(3-chlorophenyl)propyl carbamate as a reactant, instead of (2R)-2-amino-3-phenylpropyl methylcarbamate, to give 2-amino-3-(3-chlorophenyl)propyl (aminocarbonyl) carbamate; hydrochloride.

1H-NMR (DMSO-d6, 200 MHz) δ 9.82 (br, 1H), 8.20 (br, 3H), 7.37 (m, 6H), 4.26 (m, 1H), 3.96 (m, 1H), 3.70 (m, 1H), 2.95 (m, 2H)

Example 11: 2-Amino-3-(4-nitrophenyl)propyl (aminocarbonyl)carbamate and hydrochloride Salt Thereof

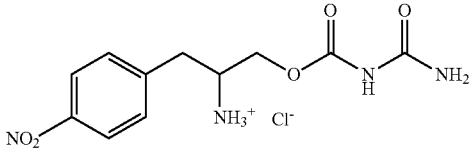 [SMILES: NC(=O)NC(=O)OCC([NH3+])Cc1ccc([N+](=O)[O-])cc1 ; [Cl-]]

The procedure given in Example 8 was followed using 2-amino-3-(4-nitrophenyl)propyl carbamate as a reactant, instead of (2R)-2-amino-3-phenylpropyl methylcarbamate, to give 2-Amino-3-(4-nitrophenyl)propyl (aminocarbonyl) carbamate; hydrochloride.

1H-NMR (DMSO-d6, 200 MHz) 9.81 (br, 1H), 8.37 (br, 3H), 8.22 (d, 2H), 7.63 (d, 2H), 7.18 (br, 2H), 4.24 (m, 1H), 4.03 (m, 1H), 3.75 (m, 1H), 3.11 (m, 2H)

Example 12: 2-Amino-3-(4-tert-butylphenyl)propyl (aminocarbonyl)carbamate and hydrochloride Salt Thereof

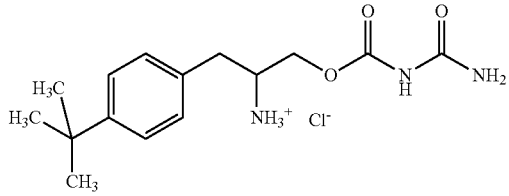 [SMILES: CC(C)(C)c1ccc(CC([NH3+])COC(=O)NC(N)=O)cc1 ; [Cl-]]

The procedure given in Example 8 was followed using 2-amino-3-(4-tert-butylphenyl)propyl carbamate as a reactant, instead of (2R)-2-amino-3-phenylpropyl methylcarbamate, to give 2-amino-3-(4-tert-butylphenyl)propyl (aminocarbonyl) carbamate; hydrochloride.

1H-NMR (DMSO-d6, 200 MHz) δ 9.78 (br, 1H), 8.33 (br, 3H), 7.25 (m, 5H), 4.21 (m, 1H), 3.99 (m, 1H), 3.60 (m, 1H), 2.92 (m, 2H), 1.27 (s, 9H)

Example 13: 2-Amino-3-(2-fluorophenyl)propyl (aminocarbonyl)carbamate and hydrochloride Salt Thereof

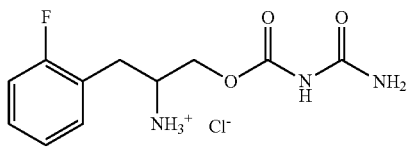 [SMILES: NC(=O)NC(=O)OCC([NH3+])Cc1ccccc1F ; [Cl-]]

The procedure given in Example 8 was followed using 2-amino-3-(2-fluorophenyl)propyl carbamate as a reactant, instead of (2R)-2-amino-3-phenylpropyl methylcarbamate, to give 2-amino-3-(2-fluorophenyl)propyl (aminocarbonyl) carbamate; hydrochloride.

1H-NMR (DMSO-d6, 200 MHz) 9.77 (br, 1H), 8.34 (br, 3H), 7.26 (m, 6H), 4.24 (dd, 1H), 4.01 (dd, 1H), 3.65 (m, 1H), 3.00 (m, 2H)

Example 14: (2R)-2-(Methylamino)-3-phenylpropyl (aminocarbonyl)carbamate and hydrochloride Salt Thereof

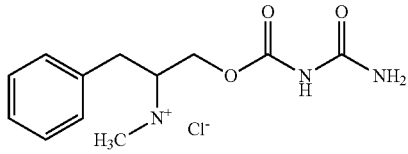 [SMILES: C[NH2+]C(COC(=O)NC(N)=O)Cc1ccccc1 ; [Cl-]]

The procedure given in Example 8 was followed using (2R)-2-(methylamino)-3-phenylpropyl carbamate as a reactant, instead of (2R)-2-amino-3-phenylpropyl methylcarbamate, to give (2R)-2-(methylamino)-3-phenylpropyl (aminocarbonyl) carbamate; hydrochloride.

1H-NMR (DMSO-d6, 200 MHz) δ 9.88 (br, 1H), 9.32 (br, 2H), 7.29 (m, 7H), 4.32 (m, 1H), 3.96 (m, 1H), 3.66 (m, 1H), 3.20 (m, 1H), 2.91 (m, 1H), 2.65 (s, 3H)

Example 15: (2R)-2-(Dimethylamino)-3-phenylpropyl(aminocarbonyl) methylcarbamate and hydrochloride Salt Thereof

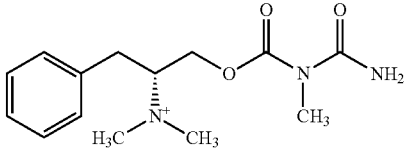

The procedure given in Example 8 was followed using (2R)-2-(dimethylamino)-3-phenylpropyl methylcarbamate as a reactant, instead of (2R)-2-amino-3-phenylpropyl methylcarbamate, to give (2R)-2-(dimethylamino)-3-phenylpropyl (aminocarbonyl) methylcarbamate; hydrochloride.

1H-NMR (DMSO-d6, 200 MHz) 11.20 (br, 1H), 7.82 (br, 1H), 7.34 (m, 6H), 4.24 (m, 2H), 3.92 (m, 1H), 3.09 (s, 3H), 2.92 (m, 2H), 2.87 (s, 6H)

Example 16: (2R)-2-Amino-3-phenylpropyl (aminocarbonyl)benzylcarbamate and hydrochloride Salt Thereof

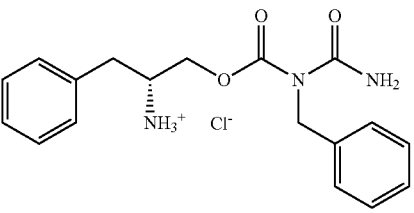 [SMILES: NC(=O)N(Cc1ccccc1)C(=O)OC[C@H]([NH3+])Cc1ccccc1 ; [Cl-]]

The procedure given in Example 8 was followed using (2R)-2-amino-3-phenylpropyl benzylcarbamate as a reactant, instead of (2R)-2-amino-3-phenylpropyl methylcarbamate, to give (2R)-2-amino-3-phenylpropyl (aminocarbonyl) benzylcarbamate; hydrochloride.

1H-NMR (DMSO-d6, 200 MHz) δ 8.15 (br, 3H), 7.92 (br, 1H), 7.58 (br, 1H), 7.28 (m, 8H), 6.93 (m, 2H), 5.03 (m, 2H), 4.22 (m, 1H), 3.89 (m, 1H), 3.62 (m, 1H), 2.84 (m, 1H), 2.65 (m, 1H

Example 17: (2R)-2-Amino-3-phenylpropyl(aminocarbonyl)ethylcarbamate and hydrochloride Salt Thereof

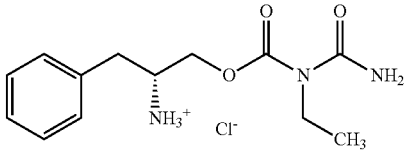

The procedure given in Example 8 was followed using (2R)-2-amino-3-phenylpropyl ethylcarbamate as a reactant, instead of (2R)-2-amino-3-phenylpropyl methylcarbamate, to give (2R)-2-amino-3-phenylpropyl (aminocarbonyl)ethylcarbamate; hydrochloride.

1H-NMR (DMSO-d6, 200 MHz) δ 8.31 (br, 3H), 7.80 (br, 1H), 7.31 (m, 6H), 4.30 (m, 1H), 4.06 (m, 1H), 3.75 (m, 3H), 3.00 (m, 2H), 1.08 (t, 3H)

Example 18: (2R)-2-Amino-3-(2-chlorophenyl)propyl(aminocarbonyl) methylcarbamate and hydrochloride Salt Thereof

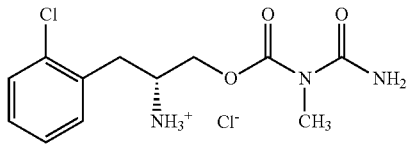 [SMILES: CN(C(N)=O)C(=O)OC[C@H]([NH3+])Cc1ccccc1Cl ; [Cl-]]

The procedure given in Example 8 was followed using (2R)-2-amino-3-(2-chlorophenyl)propyl methylcarbamate as a reactant, instead of (2R)-2-amino-3-phenylpropyl methylcarbamate, to give (2R)-2-amino-3-(2-chlorophenyl)propyl (aminocarbonyl) methylcarbamate; hydrochloride.

1H-NMR (DMSO-d6, 200 MHz) δ 8.54 (br, 3H), 7.80 (br, 1H), 7.40 (m, 6H), 4.20 (m, 2H), 3.78 (m, 1H), 3.16 (m, 2H), 3.12 (s, 3H)

Example 19: 2-Amino-3-(4-fluorophenyl)propyl (aminocarbonyl)methylcarbamate and hydrochloride Salt Thereof

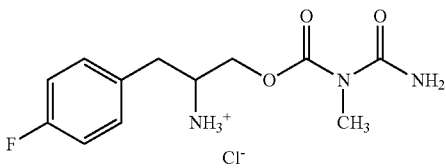 [SMILES: CN(C(N)=O)C(=O)OCC([NH3+])Cc1ccc(F)cc1 ; [Cl-]]

The procedure given in Example 8 was followed using 2-amino-3-(4-fluorophenyl)propyl methylcarbamate as a reactant, instead of (2R)-2-amino-3-phenylpropyl methylcarbamate, to give 2-amino-3-(4-fluorophenyl)propyl (aminocarbonyl)methylcarbamate; hydrochloride.

1H-NMR (DMSO-d6, 200 MHz) δ 7.10 (d, 2H), 6.92 (d, 2H), 6.01 (br, 2H), 4.3 (d, 2H), 3.6 (dd, 1H), 3.16 (s, 3H), 2.77 (d, 2H), 2.0 (br, 2H).

Example 20: (2R)-2-Amino-3-(4-chlorophenyl)propyl (aminocarbonyl) methylcarbamate and hydrochloride Salt Thereof

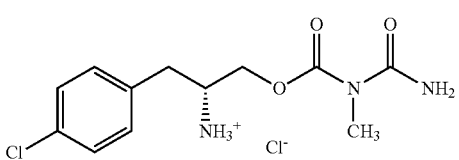 [SMILES: CN(C(N)=O)C(=O)OC[C@H]([NH3+])Cc1ccc(Cl)cc1 ; [Cl-]]

The procedure given in Example 8 was followed using (2R)-2-amino-3-(4-chlorophenyl)propyl methylcarbamate as a reactant, instead of (2R)-2-amino-3-phenylpropyl methylcarbamate, to give (2R)-2-amino-3-(4-chlorophenyl)propyl (aminocarbonyl) methylcarbamate; hydrochloride.

1H-NMR (DMSO-d6, 200 MHz) δ 7.10 (d, 2H), 6.92 (d, 2H), 6.01 (br, 2H), 4.3 (d, 2H), 3.6 (dd, 1H), 3.16 (s, 3H), 2.77 (d, 2H), 2.0 (br, 2H).

Example 21: (2R)-2-amino-3-(2,4-dichlorophenyl) propyl (aminocarbonyl) methylcarbamate and hydrochloride Salt Thereof

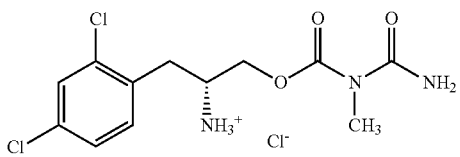 [SMILES: CN(C(N)=O)C(=O)OC[C@H]([NH3+])Cc1ccc(Cl)cc1Cl ; [Cl-]]

The procedure given in Example 8 was followed using (2R)-2-amino-3-(2,4-dichlorophenyl)propyl methylcarbamate as a reactant, instead of (2R)-2-amino-3-phenylpropyl methylcarbamate, to give (2R)-2-amino-3-(2,4-dichlorophenyl)propyl (aminocarbonyl) methylcarbamate; hydrochloride.

1H-NMR (DMSO-d6, 200 MHz) δ 8.52 (br, 3H), 7.82 (br, 1H), 7.64 (s, 1H), 7.48 (m, 3H), 4.26 (m, 1H), 4.16 (m, 1H), 3.76 (m, 1H), 3.18 (m, 5H)

Example 22: (2R)-2-Amino-3-(3,4-dichlorophenyl) propyl (aminocarbonyl) methylcarbamate and hydrochloride Salt Thereof

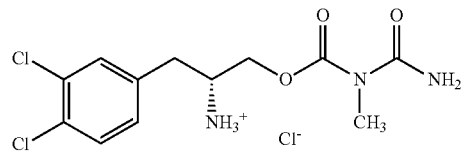 [SMILES: CN(C(N)=O)C(=O)OC[C@H]([NH3+])Cc1ccc(Cl)c(Cl)c1 ; [Cl-]]

The procedure given in Example 8 was followed using (2R)-2-amino-3-(3,4-dichlorophenyl)propyl methylcarbamate as a reactant, instead of (2R)-2-amino-3-phenylpropyl methylcarbamate, to give (2R)-2-amino-3-(3,4-dichlorophenyl)propyl (aminocarbonyl) methylcarbamate; hydrochloride.

1H-NMR (DMSO-d6, 200 MHz) δ 8.36 (br, 3H), 7.84 (br, 1H), 7.52 (m, 4H), 4.20 (m, 2H), 3.82 (m, 1H), 3.14 (s, 3H), 3.09 (m, 2H)

Example 23: (2S)-2-Amino-3-phenylpropyl (aminocarbonyl)methylcarbamate and hydrochloride Salt Thereof

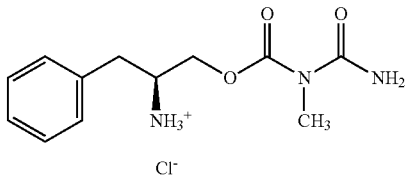 [SMILES: CN(C(N)=O)C(=O)OC[C@@H]([NH3+])Cc1ccccc1 ; [Cl-]]

The procedure given in Example 8 was followed using (2S)-2-amino-3-phenylpropyl methylcarbamate as a reactant, instead of (2R)-2-amino-3-phenylpropyl methylcarbamate, to give (2S)-2-amino-3-phenylpropyl (aminocarbonyl)methylcarbamate; hydrochloride.

1H-NMR (DMSO-d6, 200 MHz) 8.55 (br, 3H), 7.84 (br, 1H), 7.32 (m, 6H), 4.30 (dd, 1H), 4.06 (dd, 1H), 3.72 (m, 1H), 3.18 (dd, 1H), 3.14 (s, 3H), 2.90 (dd, 1H)

Example 24: 2-amino-3-phenylpropyl (aminocarbonyl)methylcarbamate and hydrochloride Salt Thereof

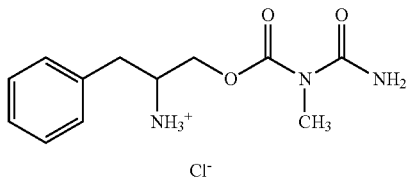 [SMILES: CN(C(N)=O)C(=O)OCC([NH3+])Cc1ccccc1 ; [Cl-]]

The procedure given in Example 8 was followed using 2-amino-3-phenylpropyl methylcarbamate as a reactant, instead of (2R)-2-amino-3-phenylpropyl methylcarbamate, to give 2-amino-3-phenylpropyl (aminocarbonyl)methylcarbamate; hydrochloride.

1H-NMR (DMSO-d6, 200 MHz) δ 8.55 (br, 3H), 7.84 (br, 1H), 7.32 (m, 6H), 4.30 (dd, 1H), 4.06 (dd, 1H), 3.72 (m, 1H), 3.18 (dd, 1H), 3.14 (s, 3H), 2.90 (dd, 1H)

Example 25: (2R)-2-Amino-3-(4-nitrophenyl)propyl (aminocarbonyl) methylcarbamate and hydrochloride Salt Thereof

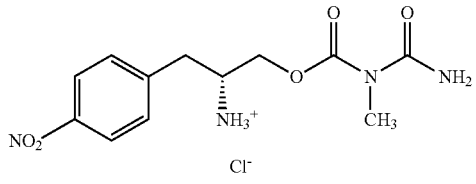 [SMILES: CN(C(N)=O)C(=O)OC[C@H]([NH3+])Cc1ccc([N+](=O)[O-])cc1 ; [Cl-]]

The procedure given in Example 8 was followed using (2R)-2-amino-3-(4-nitrophenyl)propyl methylcarbamate as a reactant, instead of (2R)-2-amino-3-phenylpropyl methylcarbamate, to give (2R)-2-amino-3-(4-nitrophenyl)propyl (aminocarbonyl) methylcarbamate; hydrochloride 1H-NMR (DMSO-d6, 200 MHz) 8.39 (br, 3H), 8.22 (d, 2H), 7.82 (br, 1H), 7.62 (d, 2H), 7.46 (br, 1H), 4.32 (m, 1H), 4.16 (m, 1H), 3.84 (m, 1H), 3.18 (m, 2H), 3.12 (s, 3H)

Example 26: (2R)-2-Amino-3-(4-methylphenyl) propyl (aminocarbonyl) methylcarbamate and hydrochloride Salt Thereof

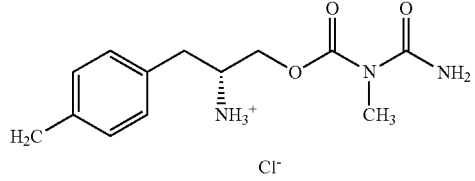 [SMILES: Cc1ccc(C[C@@H]([NH3+])COC(=O)N(C)C(N)=O)cc1 ; [Cl-]]

The procedure given in Example 8 was followed using (2R)-2-amino-3-(4-methylphenyl)propyl methylcarbamate as a reactant, instead of (2R)-2-amino-3-phenylpropyl methylcarbamate, to give (2R)-2-amino-3-(4-methylphenyl)propyl (aminocarbonyl) methylcarbamate; hydrochloride.

1H-NMR (DMSO-d6, 200 MHz) 8.34 (br, 3H), 7.82 (br, 1H), 7.42 (br, 1H), 7.16 (s, 4H), 4.26 (m, 1H), 4.05 (m, 1H), 3.65 (m, 1H), 3.13 (s, 3H), 3.04 (m, 1H), 2.82 (m, 1H), 2.28 (s, 3H)

Example 27: (2R)-2-Amino-3-(4-ethoxyphenyl) propyl (aminocarbonyl) methylcarbamate and hydrochloride Salt Thereof

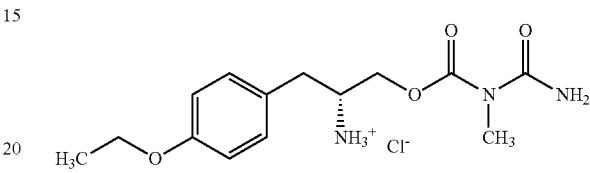

The procedure given in Example 8 was followed using (2R)-2-amino-3-(4-ethoxyphenyl)propyl methylcarbamate as a reactant, instead of (2R)-2-amino-3-phenylpropyl methylcarbamate, to give (2R)-2-amino-3-(4-ethoxyphenyl)propyl (aminocarbonyl) methylcarbamate; hydrochloride.

1H-NMR (DMSO-d6, 200 MHz) δ 8.45 (br, 3H), 7.84 (br, 1H), 7.24 (br, 1H), 7.19 (d, 2H), 6.89 (d, 2H), 4.26 (m, 1H), 4.01 (m, 3H), 3.66 (m, 1H), 3.14 (s, 3H), 3.08 (m, 1H), 2.82 (m, 1H), 1.31 (t, 3H)

Example 28: (2R)-2-Amino-4-phenylbutyl (aminocarbonyl)methylcarbamate and hydrochloride Salt Thereof

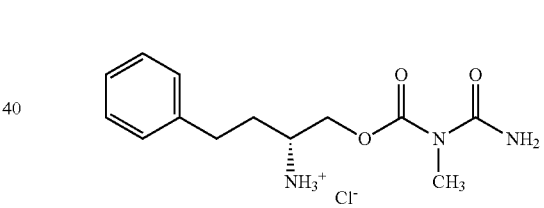

The procedure given in Example 8 was followed using (2R)-2-amino-4-phenylbutyl methylcarbamate as a reactant, instead of (2R)-2-amino-3-phenylpropyl methylcarbamate, to give (2R)-2-amino-4-phenylbutyl (aminocarbonyl)methylcarbamate; hydrochloride.

1H-NMR (DMSO-d6, 200 MHz) δ 8.41 (br, 3H), 7.85 (br, 1H), 7.42 (br, 1H), 7.27 (m, 5H), 4.42 (dd, 1H), 4.24 (dd, 1H), 3.42 (m, 1H), 3.14 (s, 3H), 2.74 (t, 2H), 1.96 (m, 2H)

Example 29: (2R)-2-Amino-3-phenylpropyl (anilinocarbonyl)carbamate and hydrochloride Salt Thereof

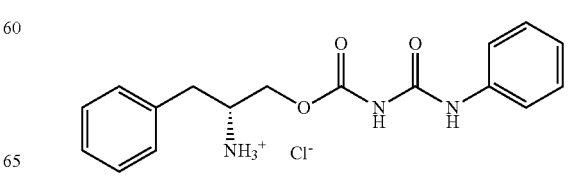

(2R)-2-amino-3-phenylpropyl carbamate (2.397 mmol) was dissolved in dichloromethane and methansulfonic acid (0.47 ml, 3 eq) and phenyl isocyanate (1.56 ml, 6 eq) was added in an ice bath. The resulting reaction mixture was stirred for 1 day. Water was added to terminate the reaction and the reaction mixture was neutralized to pH 7-8 with 1N NaOH solution. The organic layer was extracted 3 times with dichloromethane, dried over magnesium sulfate and concentrated in vacuo, to give oil. This was dissolved in dichloromethane and the solution was treated with a solution of HCl in ethyl ether. The resulting precipitate was filtered to give (2R)-2-amino-3-phenylpropyl (anilinocarbonyl)carbamate; hydrochloride.

1H-NMR (DMSO-d6, 200 MHz) δ 10.29 (br, 1H), 9.79 (br, 1H), 8.46 (br, 3H), 7.34 (m, 10H), 4.32 (m, 1H), 4.05 (m, 1H), 3.70 (m, 1H), 3.04 (m, 2H)

Example 30: Dopamine Transporter Binding Assay

Rats (SD-rat, Orient Korea, male, 200-250 g) were sacrificed by decapitation. The *striata* were removed immediately and then stored at −80° C. until used. On the day of the manipulation, the *striata* were thawed and suspended in 20 volumes of buffer containing 50 mM Tris-HCl and 120 mM NaCl (pH 7.7). The suspension then was centrifuged at 17,700 rpm for 20 minutes. The pellet was resuspended in 20 volumes of the buffer and centrifuged at 17,700 rpm for 20 minutes. This procedure was repeated once more. The pellet obtained was resuspended in a few ml of the buffer and then homogenized. The concentration of the receptor source was determined by Lowry et al., 1951, *J. Biol. Chem.* 193:265-275.

Dopamine Transporter Assay Protocol

The dopamine reuptake transporter binding assay was performed according to the methods described in Madras et al., 1989, Mol. Pharmacol. 36(4):518-524, and Javitch et al., 1984, *Mol. Pharmacol.* 26(1):35-44. The receptor source was rat striatal membranes; the radioligand was GBR12935 [prolyene-2,3-$^3$H] (DuPont-Nen, Boston, Mass.) (250 µCi), at 1.0 nM of a final concentration; for non-specific binding 1-[2-[bis(4-Fluorophenyl)methoxy]ethyl]-4-[3-phenylpropyl]piperazine dihydrochloride (GBR12909) (Research Biochemicals International, USA), a high-affinity dopamine uptake inhibitor, was used at 10 µM; reference compound was nomifensine maleate (Research Biochemicals International, USA. Reactions were carried out in 50 mM Tis-HCl (pH 7.7), containing 120 mM NaCl and at 25° C. for 45 minutes. Then the reaction was terminated by rapid vacuum filtration onto glass fiber filters. Radioactivity trapped in the filters was measured and the specific interactions of the test compound with the dopamine uptake site were determined compared to control values. The results are represented in Table 1.

TABLE 1

| Example | % inhibition (10 µM) |
|---|---|
| Example 2 | 50.1% |
| Example 3 | 40.1% |
| Example 4 | 38.4% |
| Example 6 | 20.4% |
| Example 7 | 41.2% |
| Example 8 | 20.3% |
| Example 9 | 42.8% |
| Example 14 | 35.9% |
| Example 15 | 55.5% |
| Example 16 | 20.8% |
| Example 17 | 41.2% |
| Example 18 | 17.5% |
| Example 19 | 34.3% |
| Example 21 | 31.5% |
| Example 22 | 37.0% |
| Example 24 | 45.0% |
| Example 29 | 50.7% |

As described herein, the compounds of the present disclosure were observed to have binding affinity for dopamine transporter. The results indicate that the compounds can be useful to treat or inhibit diseases caused by abnormal dopamine reuptake.

Example 31: Locomotor Activity Test

Psychostimulant activity was examined through the locomotor activity test (LMA). The LMA is a behavioral test developed to predict the efficacy of psychostimulants. The LMA is an attractive test for psychostimulants because it is sensitive and specific. All of the major classes of psychostimulants enhance ambulatory activities in the LMA, including methylphenidate, amphetamine, and many other psychostimulants.

Sixteen (16) mice (3 weeks CrjBgi:CD-1 (ICR) and 8 weeks C57BL/6) were purchased from Orient Bio Inc. (Gyeonggi-do, Korea). The mice were divided into a control group and a drug-treated group (eight (8) mice per group) by a block randomization method. Each of the group was placed in an empty cage and bred under environmental conditions of 19-25° C. with a relative humidity of 40-60% and a lighting cycle of 12 hr light/12 hr dark. Diet and water were supplied ad libitum. After one week of acclimation, the LMA test was carried out. The mice were habituated for over 1 hour in an LMA room before starting the LMA test. After habituation, the test compounds (10 or 30 mg/kg) were administered to the drug-treated group by intraperitoneal injection. At 30 minutes after i.p. dosing, LMA was measured using automated photobeams, Opto-Varimax® (Columbus Instruments, Ohio, US-확인 부탁 드립니다) and recorded on a computer. The total locomoter counts for each mouse were recorded for 10 minutes.

Statistical mean values for control and drug-treated groups were calculated and the percent changes from control were determined. Percent changes from control-revealed as % reduction-of some of the compounds of the instant disclosure are presented in Table 2.

TABLE 2

| Example | % ambulation |
|---|---|
| Example 2 | 118.7% (30 mg/kg, ip) |
| Example 3 | 291.5% (30 mg/kg, ip) |
| Example 4 | 242.6% (30 mg/kg, ip) |
| Example 8 | 186.4% (30 mg/kg, ip) |
| Example 15 | 202.2% (10 mg/kg, ip) |

As described above, the compounds of the present disclosure were observed to have psychostimulant efficacy which is useful to treat a dopamine reuptake-related disease such as ADHD.

What is claimed is:

1. A compound of 2-amino-3-phenylpropyl(aminocarbonyl)carbamate or a pharmaceutically acceptable salt or stereoisomer thereof.

2. The compound of claim 1, wherein the pharmaceutically acceptable salt is a hydrochloride salt.

3. The compound of claim 1, wherein the compound is (2R)-2-amino-3-phenylpropyl(aminocarbonyl)carbamate, or a pharmaceutically acceptable salt thereof.

4. The compound of claim 3, wherein the pharmaceutically acceptable salt is a hydrochloride salt.

5. A pharmaceutical composition comprising a compound or a pharmaceutically acceptable salt or stereoisomer thereof of claim 1 and a pharmaceutically acceptable carrier.

6. The pharmaceutical composition of claim 5, wherein the pharmaceutically acceptable salt is a hydrochloride salt.

7. The pharmaceutical composition of claim 5, wherein the compound is (2R)-2-amino-3-phenylpropyl(aminocarbonyl)carbamate, or a pharmaceutically acceptable salt thereof.

8. The pharmaceutical composition of claim 7, wherein the pharmaceutically acceptable salt is a hydrochloride salt.

9. The pharmaceutical composition of claim 5, which is an oral formulation.

10. The pharmaceutical composition of claim 5, further comprising an active ingredient which is effective to treat ADHD.

11. A method for inhibiting dopamine reuptake comprising:
    administrating to a subject in need thereof a therapeutically effective amount of 2-amino-3-phenylpropyl(aminocarbonyl)carbamate or a pharmaceutically acceptable salt thereof.

12. The method of claim 11, wherein the pharmaceutically acceptable salt is a hydrochloride salt.

13. The method of claim 11, wherein the compound is (2R)-2-amino-3-phenylpropyl(aminocarbonyl)carbamate, or a pharmaceutically acceptable salt thereof.

14. The method of claim 13, wherein the pharmaceutically acceptable salt is a hydrochloride salt.

15. The method of claim 11, which is for the treatment of a central nervous system disease.

16. The method of claim 11, which is for the treatment of attention deficit hyperactivity disorder (ADHD).

17. The method of claim 11, further comprising one or more additional therapeutic agents.

18. The method of claim 17, wherein the one or more additional therapeutic agents are independently selected from the group consisting of amphetamine, methylphenidate, dextroamphetamine, dexmethylphenidate, and lisdexamfetamine.

* * * * *